United States Patent [19]

Ward

[11] 4,291,042
[45] Sep. 22, 1981

[54] ANTIDEPRESSANT PIPERIDINE DERIVATIVES

[75] Inventor: Terence J. Ward, Cippenham, England

[73] Assignee: John Wyeth & Brother Limited, Maidenhead, England

[21] Appl. No.: 113,938

[22] Filed: Jan. 21, 1980

[30] Foreign Application Priority Data

Jan. 26, 1979 [GB] United Kingdom ............... 02824/79
Oct. 16, 1979 [GB] United Kingdom ............... 35865/79

[51] Int. Cl.[3] .................. A61K 31/445; C07D 409/14; C07D 401/14
[52] U.S. Cl. .................. 424/267; 424/258; 424/262; 546/110; 546/113; 546/114; 546/115; 546/116; 546/141; 546/142; 546/196; 546/198; 546/200; 546/201; 546/202; 546/270; 546/272; 546/273
[58] Field of Search ............... 546/201, 198, 200, 141, 546/142, 110; 424/267, 258, 262

[56] References Cited

U.S. PATENT DOCUMENTS 4,000,287 12/1976 Werner ..................... 546/200 X
4,053,615 10/1977 Boyle et al. ................ 546/200 X

FOREIGN PATENT DOCUMENTS 1425578 2/1976 United Kingdom ............. 546/200

OTHER PUBLICATIONS

Chemical Abstracts, 83:193099j (1975) [German OLS 2,503,816, Derible et al., 7/31/75].
Chemical Abstracts, 71:61120b (1970) [Domnina, E., et al., Khim. Atsetilena 1968, 203-207].
Houlihan, W. (Editor), indoles, Wiley Interscience, New York, Part 2 (1972), pp. 475-479, and Part 3 (1979), p. 180.

Primary Examiner—Richard A. Schwartz
Attorney, Agent, or Firm—Richard K. Jackson

[57] ABSTRACT

Compounds of formula:

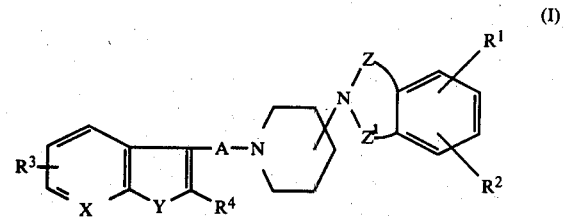

(I)

and pharmaceutically acceptable acid addition or quaternary ammonium salts thereof wherein the piperidine ring is substituted in the 3 or 4 position; X represents =CH— or =N—; Y represents —NR[5]—, —O— or —S— wherein R[5] is hydrogen or lower alkyl; A is lower alkylene or hydroxy lower alkylene, Z and Z[1] independently represent

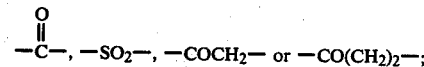

Z may also represent —CH$_2$—, —(CH$_2$)$_2$—, —CHMe— or —CMe$_2$—; R[1], R[2], R[3] independently represent hydrogen, halogen, lower alkyl, lower alkoxy, nitro, amino, lower alkylamino, trifluoromethyl, lower-alkanoylamino, hydroxy or aryl lower alkoxy; or R[1] and R[2] when adjacent together with the carbons to which they are attached form a six membered carbocyclic ring; and R[4] represents hydrogen or lower alkyl, are disclosed which possess psychotropic activity and are useful as anti-depressants.

25 Claims, No Drawings

ANTIDEPRESSANT PIPERIDINE DERIVATIVES

This invention relates to new piperidine derivatives, to processes for preparing them and to pharmaceutical compositions containing them.

In our U.K. Pat. No. 1,425,578 we have described and claimed compounds of the general formula:

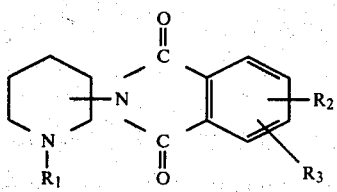 (A)

and their pharmaceutically acceptable acid addition salts, where $R_1$ represents a hydrogen atom, an alkyl group, an aralkyl group or an alkyl group substituted by a heterocyclyl group; $R_2$ and $R_3$, which may be the same or different, represent a hydrogen atom, a halogen atom (for instance, chlorine or bromine), a trifluoromethyl group, a lower alkyl group, a lower alkoxy group, a nitro group, a hydroxy group, an amino group, a monoalkylamino group (for instance, a monomethylamino group) or a dialkylamino group (for instance, a dimethylamino or diethylamino group).

According to U.K. Pat. No. 1,425,578 the compounds of formula A show anti-convulsant activity and in some cases anti-inflammatory activity or antiarrhythmic activity when tested on warm blooded animals.

We have now surprisingly found that certain compounds falling within the general formula A of U.K. Pat. No. 1,425,578, but not specifically exemplified form part of a class of compounds exhibiting psychotropic activity as measured by inhibition of uptake of 5-hydroxytryptamine in brain slices. The compounds are therefore useful as anti-depressants. The present invention concerns this new class of compounds and their use.

Accordingly this invention provides new compounds having the general formula

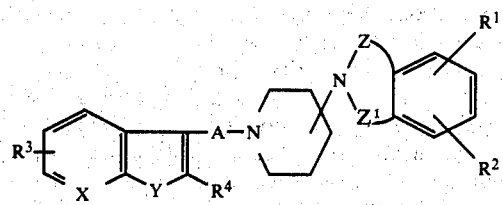 (I)

and their pharmaceutically acceptable acid addition and quaternary ammonium salts, wherein the piperidine ring is substituted in the 3 or 4 position; X represents =CH— or =N—; Y represents —NR$^5$—, —O— or —S— wherein R$^5$ is hydrogen or lower alkyl; A is lower alkylene or hydroxy lower alkylene, Z and $Z^1$ independently represent

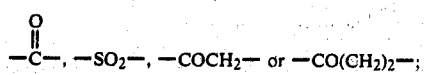

Z may also represent —CH$_2$—, —(CH$_2$)$_2$—, —CHMe— or —CMe$_2$—; $R^1$, $R^2$, $R^3$, independently represent hydrogen, halogen, lower alkyl, lower alk- oxy, nitro, amino, lower alkylamino, trifluoromethyl, lower alkanoylamino, hydroxy or aryl lower alkoxy; or $R^1$ and $R^2$ when adjacent, together with the carbons to which they are attached form a six membered carbocyclic ring; and $R^4$ represents hydrogen or lower alkyl.

The term "aryl" as used herein means a carbocyclic ring having aromatic character.

The term "lower" as used herein in connection with such groups as "alkyl" and "alkylene" denotes that the group contains up to 6 carbon atoms, preferably not more than 4 carbon atoms.

Examples of A are straight chain alkylene groups such as —CH$_2$—, —CH$_2$—CH$_2$—, —(CH$_2$)$_3$— and —(CH$_2$)$_4$—, and branched chain alkylene groups such as

—CH—, —CH—CH$_2$—,
   |          |
   CH$_3$    CH$_3$

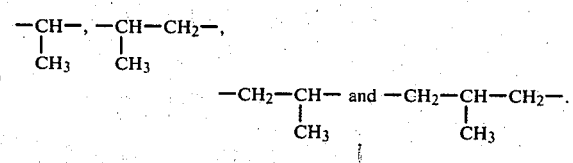

Examples of hydroxy lower alkylene groups for A are —CHOH—CH$_2$—, —CH$_2$—CHOH—CH$_2$— and —CHOHCH$_2$CH$_2$—. Preferably A is —CH$_2$— or —CH$_2$CH$_2$—.

Examples of lower alkyl groups for $R^1$, $R^2$, $R^3$, $R^4$ and $R^5$ are methyl, ethyl, n-propyl, i-propyl, n-butyl, n-pentyl and n-hexyl. Preferred lower alkyl groups are methyl and ethyl.

Examples of $R^1$, $R^2$ or $R^3$ when halogen are fluorine, chlorine or bromine.

Examples of lower alkoxy groups for $R^1$, $R^2$ and $R^3$ are methoxy, ethoxy, n-propoxy, isopropoxy and n-butoxy.

Preferred lower alkoxy groups are methoxy and ethoxy. $R^3$ when aryl lower alkoxy is preferably benzyloxy. Preferred values for Z and $Z^1$ are —CO—. Preferably X is =CH—. Preferably Y is —NH—. Preferably the piperidine ring is substituted in the 4-position. Preferably $R^1$ is H, Cl or NH$_2$.

Preferred compounds of the invention are 2-(1-[indol-3-ylmethyl]piperid-4-yl-1H-isoindole-1,3-(2H)-dione (compound I); 2-(1-[2-(indol-3-yl)ethyl]piperid-4-yl)-1H-isoindol-1,3-(2H)-dione (compound II), and 5-amino-2-(1-[2-(indol-3-yl)ethyl]piperid-4-yl)-1H-isoindole-1,3-(2H)-dione (compound III).

Examples of acid addition salts are those formed from inorganic and organic acids and in particular pharmaceutically acceptable acid addition salts such as the hydrochloride, hydrobromide, hydroiodide, sulphate, nitrate, phosphate, sulphonate (such as the methanesulphonate and p-toluenesulphonate), acetate, maleate, citrate, fumarate, tartrate, malonate and formate.

The compounds of formula I were tested for the ability to inhibit noradrenaline and 5-hydroxytryptamine uptake in brain slices in the following standard test:

The effects of test compounds on the neuronal uptake of noradrenaline into slices of cerebral cortex prepared from rat brain is determined according to the method described by Snyder, Green and Hendley, Kinetics of H$^3$—norepinephrine accumulation into slices from different regions of the rat brain (J.Pharm. exp. Therap. 164: 90-102) (1968). The effects of test compounds on the uptake of 5-hydroxytryptamine is obtained in a similar manner except that H³5-hydroxytryptamine is used in place of H³noradrenaline. Concentration-response curves are obtained both for the test compound and for the standard agent, imipramine. The potency of each test compound is expressed in proportion to that of imipramine. Thus, the potency ratio for the test compound =
$$\frac{\text{Molar concentration of imipramine giving 50\% inhibition of NA (or 5HT) uptake}}{\text{Molar concentration of test drug giving 50\% inhibition of NA (or 5HT) uptake}}$$

Compounds not achieving 50% inhibition are considered inactive.

In such a test the compounds I, II and III above and a compound from U.K. Pat. No. 1,425,578, namely 2-(1-benzylpiperid-4-yl)-1H-isoindol-1,3-(2H)-dione (B) gave the following results:

| Compound | Potency Ratio (imipramine = 1.0) | |
|---|---|---|
| | Nora-drenaline | 5-hydroxytryptamine |
| I | 0.01 | 9.5 |
| II | 0.06 | 8.3 |
| III | inactive | 11.0 |
| | inactive | inactive |

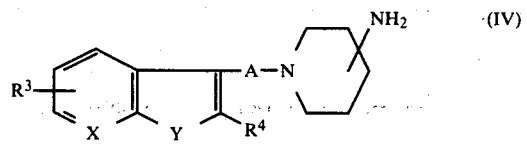

Thus both compounds I, II and III are potent inhibitors of 5-HT (hydroxytryptamine) uptake and very weak inhibitors of noradrenaline uptake. The compound 2-(1-benzylpiperid-4-yl)-1H-isoindol-1,3-(2H)-dione was inactive in the test.

Compounds of formula I were also tested for their ability to inhibit p-chloroamphetamine induced hyperactivity. The following procedure was used:

Three groups of 4 female mice (20–24 g) received the test compounds (50 mg/kg po) and a fourth group the requisite volume of vehicle. Thirty minutes later all the animals are given 20 mg/kg p-chloroamphetamine (pCA) ip. The grouped mice are placed immediately in square plastic cages in activity monitors and their motor activity recorded over the period 10–30 minutes post pCA. This procedure is repeated three more times so that four groups of mice are used per treatment and each activity monitor is used with all treatments in turn. The inhibition of pCA induced hyperactivity is calculated thus:

$$\frac{C-T}{C} \cdot 100\%$$

where
C = mean activity of control groups 10–30 minutes post pCA.
T = mean activity of treated groups 10–30 minutes post pCA.

This test is used as an in vivo screen for detection of 5-hydroxytryptamine uptake inhibitors.

Compounds giving >50% inhibition are considered of special interest. In such a test the following compounds were particularly active:

| Compound | % Inhibition of pCA induced hyperactivity |
|---|---|
| 2-(1-[indol-3-ylmethyl]piperid-4-yl)-1H-isoindole-1,3-(2H)-dione | 53% |
| 2-(1-[indol-3-ylmethyl]piperid-4-yl)-1,2-benzisothiazolin-3-one-1,1-dioxide | 56% |
| 5-chloro-2-(1-[2-(indol-3-yl)ethyl]piperid-4-yl)-1H-isoindole-1,3-(2H)-dione | 94% |
| 5-chloro-2-[1-(indole-3-ylmethyl)-piperid-4-yl]-1H-isoindole-1,3-(2H)-dione | 63% |

This invention also provides processes for preparing compounds of formula I or acid addition or quaternary ammonium salts thereof. In general the compounds of formula I are prepared by building up the molecule from the appropriate starting materials by known reactions. Accordingly a first process for preparing a compound of formula I comprises reacting a compound of formula II

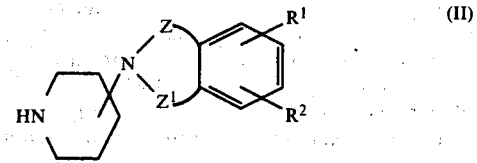

wherein $R^1$, $R^2$, Z and $Z^1$ are as defined in connection with formula I, with a compound of formula III

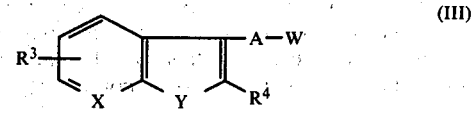

wherein $R^3$, $R^4$, A, X and Y are as defined above and W represents a leaving group, such as halogen (e.g. chlorine, bromine or iodine), an organic sulphonyloxy radical (e.g. tosyloxy, mesyloxy), a disubstituted amino radical (such as dimethylamino), a trisubstituted ammonium radical (such as trimethyl ammonium, $\oplus NMe_3$). Where the leaving group is a halogen or an organic sulphonyloxy radical the reaction is preferably carried out in the presence of base, e.g. potassium carbonate, triethylamine; otherwise the reaction may be carried out by heating in the presence of an inert solvent, e.g. toluene.

A second general process for preparing compounds of formula I (wherein Z is —CO—, —COCH₂—, —SO₂— or —CO(CH₂)₂—) comprises reacting a compound of formula IV wherein $R^3$, $R^4$, A, X and Y are as defined above, with an acid of formula

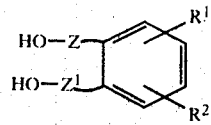

or a reactive derivative thereof, wherein $Z^1$, $R^1$ and $R^2$ are as hereinbefore defined and Z is as defined immediately above. Examples of reactive derivatives of the acid of formula (V) are di-acid halides (e.g. chloride) and acid anhydrides. Such reactions may be brought to completion by employing a dehydrating agent (e.g. acetic anhydride). Other examples of reactive derivatives are alkoxycarbonylimides of general formula:

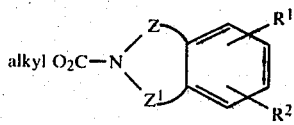

A further process for preparing a compound of formula I comprises reducing a compound of formula VI or VII

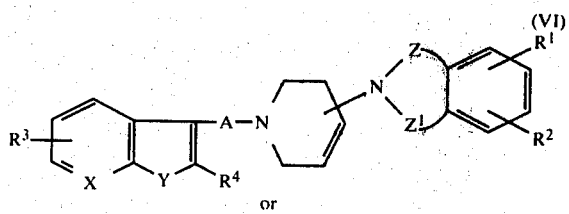

or

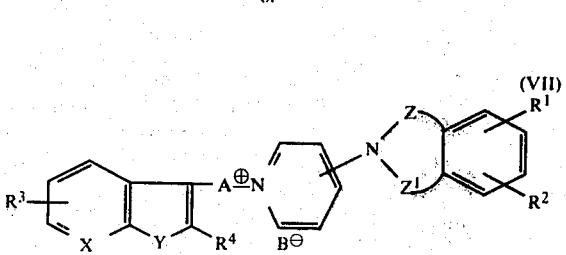

wherein $R^1$, $R^2$, $R^3$, $R^4$, X, Y, Z and $Z^1$ are as hereinbefore defined and $B^\ominus$ represents an anion, e.g. a halide ion, for example by catalytic hydrogenation, e.g. in the presence of Raney nickel or platinum catalyst. The reduction may also be effected by a process described and claimed in our U.K. Pat. No. 1,542,137. Such a reduction process employs an alkali metal borohydride in a secondary alkanol having 3–5 carbon atoms, e.g. isopropanol.

Yet a further process for preparing a compound of formula I comprises reacting a compound of formula VIII

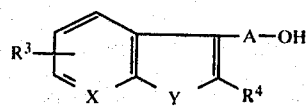

wherein X, Y, A, $R^3$ and $R^4$ are as hereinbefore defined with a compound of formula II, in the presence of a catalyst, e.g. Raney nickel.

Compounds of formula I wherein the piperidine ring is substituted in the 4-position may also be prepared by a process which comprises reacting a compound of formula

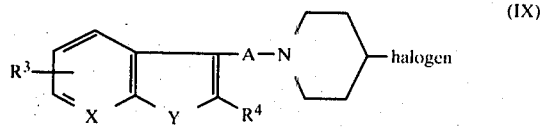

with an alkali metal salt of a compound of formula

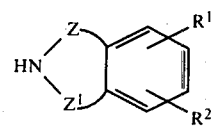

in which formulae A, X, Y, Z, $Z^1$, $R^1$, $R^2$, $R^3$ and $R^4$ are as hereinbefore defined.

Examples of halogen in the compound of formula IX are chlorine and bromine. Examples of alkali metal salts of the compound of formula X are the potassium and sodium salts.

When it is desired to prepare a compound of formula I wherein A is methylene and Y is $-NR^5-$ as defined above then such a compound can be prepared by reacting a compound of formula

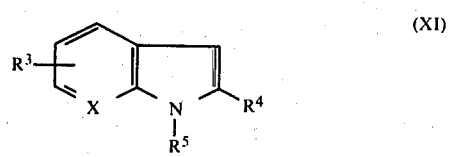

with formaldehyde and a piperidine derivative of formula II

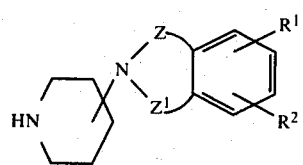

in which formulae X, Z, $Z^1$, $R^1$, $R^2$, $R^3$, $R^4$ and $R^5$ are as hereinbefore defined. The formaldehyde used in the above reaction may be in the form of a solution in an inert solvent or as paraformaldehyde.

Once a compound of formula I has been prepared then that compound may be converted in known manner to other compounds of formula I. For example when $R^5$ is hydrogen then that compound may be alkylated to produce a compound of formula I wherein $R^5$ is lower alkyl e.g. using sodium hydride and methyliodide. When $R^3$ is lower alkoxy or aryl lower alkoxy dealkylation produces a corresponding compound of formula I wherein $R^3$ is hydroxy. When any of $R^1$, $R^2$ and $R^3$ is nitro then reduction (e.g. catalytic hydrogenation) will convert the nitro group to an amino group.

Compounds of formula I wherein Z is $-CH_2-$ or $-(CH_2)_2-$ may be prepared by reducing, e.g. using zinc dust in glacial acetic acid, a corresponding compound of formula I wherein Z is $-CO-$ or $-COCH_2-$.

The aforementioned processes may also include the step of conversion of an acid addition salt into the free base form or vice versa. Quaternisation of the tertiary nitrogen of the piperidine ring may be included as an optional after step, e.g. using alkyl or aryl lower alkyl halides, e.g. methyl iodide, benzyl chloride.

Starting materials used in the above mentioned processes are known compounds or may be prepared by analogous processes. For example, a compound of formula II may be prepared by reducing the corresponding compound of formula XII

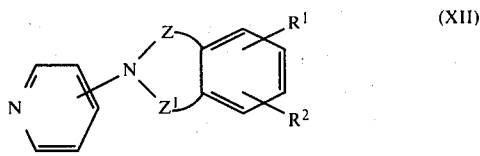
(XII)

using for example catalytic hydrogenation. Compounds of formula XII may be prepared by reacting a 4-halopyridine with an alkali metal salt of compound of formula X, or by reacting a 3 or 4-aminopyridine with a di-acid or reactive derivative of formula V.

Compounds of formula VII may be prepared by reacting a compound of formula III wherein W is halogen, especially bromine, with a compound of formula XII.

Compounds of formula VI may be prepared by reducing, e.g. using sodium borohydride in methanol, a compound of formula VII.

Compounds of formula II wherein Z is —CO— or —COCH$_2$— may be reduced, e.g. using zinc dust in glacial acetic acid, to give corresponding compounds of formula II wherein Z is —CH$_2$— or —(CH$_2$)$_2$—.

A further aspect of this invention includes a method of treating depression in animals which comprises administering an effective amount of a compound of formula I as hereinbefore defined.

This invention also includes pharmaceutical compositions containing as active ingredient an active compound of formula I as above defined. The active compound may be finely comminuted if desired. In addition to the active ingredient, the compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient.

Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxy-methyl cellulose solution, or in a suitable oil, for instance arachis oil. Liquid pharmaceutical compositions which are sterile solutions or suspensions can be utilized by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

This invention also includes compounds of formula VI and VII as hereinbefore defined which are intermediates to compounds of formula I.

The following examples illustrate the invention.

EXAMPLE 1

2-(1-[Indol-3-ylmethyl]piperid-4-yl)-1H-isoindole-1,3-(2H)-dione

Formaldehyde (0.84 cm$^3$, 40% aq. w/v, 11.3 mmol) was added to a stirred and cooled mixture of indole (1.32 g, 11.3 mmol), 2-(piperid-4-yl)-1H-isoindol-1,3-(2H)-dione, hydrochloride (3.0 g, 11.3 mmol), and sodium acetate (0.93 g, 11.3 mmol) in glacial acetic acid (10 cm$^3$). The suspension was stirred at room temperature for 5 hours, then poured into water and a gummy precipitate filtered off. The mother liquors were basified by addition of 0.880 ammonia to precipitate the title compound, which was collected and dried (2.52 g, 62.4%).

The hydrochloride was precipitated from a suspension of the base in hot ethanol by addition of ethanolic HCl. Two recrystallisations from ethanol gave the hydrochloride as pale pink crystals, m.p. 171°–174° C.

Analysis Found: C, 63.39; H, 5.67; N, 10.37%; C$_{22}$H$_{21}$N$_3$O$_2$.HCl.1.25H$_2$O requires C, 63.15; H, 5.90; N, 10.04%.

EXAMPLE 2

2-(1-[2-(Indol-3-yl)ethyl]piperid-4-yl)-1H-isoindol-1,3-(2H)-dione

Phthalic anhydride (2.96 g, 0.02 mol, finely ground) and 4-amino-1-[2-(indol-3-yl)ethyl]piperidine (4.86 g, 0.02 mol) were suspended in chloroform (40 cm$^3$) and the suspension stirred at room temperature overnight. The solvent was then evaporated and acetic anhydride (40 cm$^3$) added to the residue. This mixture was heated on a steam bath for 2 hours then the solvent removed in vacuo to give a glassy solid which was dissolved in very dilute aqueous acetic acid. Basification of the solution with 0.880 ammonia gave the title compound as a gum which solidified on trituration with methanol. (4.31 g, 57.8%). A suspension of the base in ethanolic HCl was stirred overnight to give the hydrochloride, m.p. 252°–260° after extensive decomposition above 240° C.

Analysis: Found: C, 66.65; H, 6.06; N, 10.10%. $C_{23}H_{23}N_3O_2.HCl.\frac{1}{4}H_2O$ requires C, 66.66; H, 5.90; N, 10.14%.

EXAMPLE 3

2-(1-[Indol-3-ylmethyl]piperid-4-yl)-1,2-benzisothiazolin-3-one-1,1-dioxide

Formaldehyde (0.4 cm$^3$, 40% aqu.soln.) was added to a mixture of indole (0.6 g, 0.005 mol), 2-(piperid-4-yl)-1,2-benzisothiazoline-3-one-1,1-dioxide, hydrochloride (1.5 g, 0.005 mol) and methanol (10 cm$^3$). The mixture was warmed sufficiently to give a clear solution and then allowed to stand without further heating for 2 hours. The clear solution was then evaporated, and the residual water removed by successive evaporation of the residue with ethanol to give a gum. The gum was dissolved in methanol and allowed to stand in ice whereupon the crystalline title compound separated (1.7 g, 79%) as the hydrochloride. Recrystallisation twice from aqueous methanol (80% methanol) gave 1.3 g of the title compound as the hydrochloride hemihydrate, m.p. 214°–215° C.

Analysis: Found: C, 57.63; H, 5.18; N, 9.24. $C_{21}H_{21}N_3O_3S.HCl.0.5H_2O$ requires C, 57.20; H, 5.26; N, 9.53%.

EXAMPLE 4

2-[1-(2-[Indol-3-yl]ethyl)piperid-4-yl]-1,3-(2H,4H)-isoquinolinedione

4-Amino-1-[2-(indol-3-yl)ethyl]piperidine (2.43 g, 0.01 mol) and homophthalic acid (1.80 g, 0.01 mol) were heated at 160° (external temperature) for 3 hours then cooled to room temperature, giving a glass. This was dissolved in refluxing methanol and a small quantity of ethanol then cooled at 5° C. overnight. The title compound was deposited as a tacky solid which was collected and dried (0.82 g, 21.2%). The hydrochloride was formed by treatment of the base overnight with ethereal HCl, m.p. 186°–188°.

Analysis: Found: C, 64.84; H, 6.18; N, 9.15. $C_{24}H_{25}N_3O_2.HCl.\frac{1}{2}H_2O$ requires C, 64.57; H, 6.43; N, 9.41%.

EXAMPLE 5

2,3-Dihydro-2-[1-(indol-3-ylmethyl)piperid-4-yl]-1H-isoindol-1-one (a) Indole (0.51 g, 4.36 mmol) and 4-(2-phthalimidino)-piperidine acetate (1.2 g, 4.35 mmol) were suspended in glacial acetic acid (5 cm$^3$) and aqueous formaldehyde (0.33 cm$^3$, 40% aq w/v, 4.35 mmol) was added at room temperature with stirring. The reaction mixture was stirred until homogeneous then allowed to stand. After 5 hours the solution was poured into water and filtered. The filtrate was basified by addition of conc. ammonia to precipitate the title compound. This was collected and dried. (1.30 g, 86.7%).

The hydrochloride was formed by trituration of the base overnight with ethereal hydrogen chloride, m.p. softens above 190° C.

Analysis: Found: C, 65.93; H, 6.47; N, 10.68%. $C_{22}H_{23}N_3O.HCl.H_2O$ requires C, 66.07; H, 6.55; N, 10.51%.

(b) 4-(2-Phthalimidino)piperidine acetate was prepared by the following procedure: 4-(2-Phthalimido)-piperidine, hydrochloride (2.67 g 0.01 mol) was dissolved in glacial acetic acid (25 cm$^3$) at 70° C. Zinc dust (3.5 g, 0.055 g atoms) was added all at once, with stirring, and the reaction mixture heated to reflux. Refluxing was continued for 5 hours, then unchanged zinc filtered off and the reaction mixture left overnight. Acetic acid was evaporated off leaving a solid which was dissolved in water. Addition of aqueous sodium bicarbonate precipitated 4-(2-phthalimidino)piperidine acetate which was collected and dried (1.54 g).

EXAMPLE 6

5,6-Benzo-2-(1-[2-(indol-3-yl)ethyl]piperid-4-yl)-1H-isoindol-1,3-(2H)-dione.

An intimate mixture of 4-amino-1-[2-(indol-3-yl)ethyl]piperidine (1.21 g, 5 mmol) and naphthalene-2,3-dicarboxylic acid (1.08 g, 5 mmol) was heated at 175° C. for 2 hours. The melt was then extracted under reflux with ethanol (15 cm$^3$) until the product formed a crystalline solid. The extract was cooled and the solid collected by filtration to give the title compound 1.6 g (80%). The base was dissolved in warm dimethylformamide and acidified with ethanolic hydrogen chloride to precipitate the hydrochloride, which was recrystallized twice from aqueous DMF (1:1) to give 0.8 g (36.4%), m.p. 280°–84° C.

Analysis: Found: C, 68.46; H, 5.89; N, 8.55%. $C_{27}H_{25}N_3O_2.HCl.\frac{1}{4}H_2O$ requires C, 68.49; H, 5.85; N, 8.87.

EXAMPLE 7

2-[1-(3-[Indol-3-yl]propyl)piperid-4-yl]-1H-isoindole-1,3-(2H)-dione

3-Tosyloxypropylindole (1.65 g, 5 mmol), 4-phthalimidopiperidine, hydrochloride (1.33 g, 5 mmol) and potassium carbonate (1.5 g, 10.9 mmol) were ground together and then heated at 110° C. for 2 hours. The mixture was triturated twice with water under reflux followed by ethanol, giving the title compound as a pale brown solid (0.39 g, 20%), m.p. 187°–190° C.

The base was suspended in boiling ethanol and ethanolic HCl added to give an acidic solution. This crystallised on cooling in ice. The hydrochloride was collected and recrystallised from aqueous ethanol, giving pale brown shiny plates. m.p. 255°–260° C., with extensive decomposition above 220° C.

Analysis: Found: C, 67.96; H, 6.42; N, 9.66%. $C_{24}H_{25}N_3O_2.HCl$ requires C, 68.00; H, 6.18; N, 9.91.

EXAMPLE 8

5-Chloro-2-(1-[2-(indol-3-yl)ethyl]piperid-4-yl)-1H-isoindole-1,3-(2H)-dione.

4-Amino-1-[2-(indol-3-yl)ethyl]piperidine (3.86 g, 15.9 mmol) was dissolved in warm methyl cyanide (50 cm$^3$) and a solution of 4-chlorophthalic anhydride (2.9 g, 15.9 mmol) in methyl cyanide (20 cm$^3$) was added dropwise with stirring, to precipitate a solid. The suspension was stirred at room temperature overnight then cooled briefly in ice and the solid collected. This crude material was heated in acetic anhydride (70 cm$^3$) for 2½ hours then the solvent was evaporated. The residue was dissolved in methanol, to destroy excess acetic anhydride, then the methanol was evaporated. The residue was dissolved in very dilute aqueous acetic acid and the solution was basified by addition of conc. ammonia to precipitate a gum. The supernatant layer was decanted and the gum triturated with boiling ethanol and cooled in ice to give crystals of the title compound (2.82 g, 43.6%), m.p. 188°–190° C.

The base was suspended in boiling ethanol, acidified by addition of ethanolic HCl, filtered and cooled in ice, giving a gum. This was recrystallised twice from ethanol to give the pure hydrochloride salt, m.p. 274°–277° C. (dec).

Analysis: Found: C, 62.14; H, 5.31; N, 9.76%. $C_{23}H_{22}N_3O_2Cl \cdot HCl$ requires C, 62.17; H, 5.22; N, 9.46%.

EXAMPLE 9

2-[1-(2-[Indol-3-yl]ethyl)piperid-4-yl]-5-methyl-1H-isoindole-1,3-(2H)-dione.

4-Amino-1-[2-(indol-3-yl)ethyl]piperidine (1.22 g, 5 mmol) was dissolved in warm methyl cyanide (50 cm$^3$) and a solution of 4-methylphthalic anhydride (0.81 g, 5 mmol) in methyl cyanide (10 cm$^3$) was added dropwise with stirring to precipitate a white solid. The suspension was stirred overnight then the solid collected and heated in acetic anhydride (40 cm$^3$) for 2 hours on a steam bath. The acetic anhydride was evaporated. The residue was dissolved in very dilute aqueous acetic acid and the solution basified by addition of conc. ammonia to give a gum. The mother liquor was decanted and the gum recrystallised from ethanol to give crystals of the title compound (0.53 g, 27.3%).

The base was suspended in refluxing propan-2-ol, and the suspension acidified with ethanolic HCl to give a solution. Cooling in ice gave the hydrochloride as a gum. This was recrystallised from ethanol, m.p. 160°–163° C. as the monohydrate.

Analysis: Found: C, 65.50; H, 6.10; N, 9.13%. $C_{24}H_{25}N_3O_2 \cdot HCl \cdot H_2O$ requires C, 65.23; H, 6.39; N, 9.51%.

EXAMPLE 10

2-[1-(2-[Indol-3-yl]ethyl)piperid-4-yl]-5-nitro-1H-isoindole-1,3-(2H)-dione.

4-Amino-1-[2-(indol-3-yl)ethyl]piperidine (1.22 g, 5 mmol) was dissolved in refluxing acetonitrile (20 cm$^3$) and a solution of 4-nitrophthalic anhydride (0.96 g, 5 mmol) in acetonitrile (10 cm$^3$) was added dropwise with stirring to precipitate a yellow gum. The mixture was refluxed for a further 2–3 minutes then cooled in ice. The precipitated material was collected and heated in acetic anhydride on a steam bath for ½ hour. The solvent was evaporated. Methanol was added to the residue and evaporated to destroy excess acetic anhydride. The residue was then dissolved in very dilute aqueous acetic acid and insoluble material filtered off. The filtrate was basified by addition of conc. ammonia to precipitate a gum, which was triturated with methanol under reflux to give the title compound as a bright orange solid (0.44 g, 21%).

The base was suspended in hot ethanol and the mixture acidified with ethanolic HCl, filtered and cooled in ice to give the hydrochloride 1¼ hydrate, m.p. 194°–195° C.

Analysis: Found: C, 57.46; H, 5.02; N, 11.93%. $C_{23}H_{22}N_4O_4 \cdot HCl \cdot 1\frac{1}{4}H_2O$ requires C, 57.86; H, 5.38; N, 11.74%.

EXAMPLE 11

5-Amino-2-(1-[2-(indol-3-yl)ethyl]-piperid-4-yl)-1H-isoindole-1,3-(2H)-dione.

The title compound of Example 10 (0.99 g, 2.37 mmol) was dissolved in ethanol/acetic acid and hydrogenated over 5% Pd/C at 20° C. and 40 psi. Uptake ceased after 6 hours. The catalyst was filtered off and the filtrate evaporated. The oily residue was dissolved in water and basified by addition of conc. ammonia to give a mixture of solid and gum. The gum was removed by hand and the solid collected and dried (0.54 g, 58.7%).

The base was suspended in refluxing ethyl acetate and isopropanol was added dropwise until most of the material had dissolved. The mixture was filtered and ethereal HCl added to the filtrate, which crystallised at once. Further ethyl acetate was added until the suspension was mobile, then the pH was checked to be 1 and the suspension stirred overnight at room temperature. The title compound as the dihydrochloride salt was collected and dried, m.p. 180°–183° C. (dec).

Analysis: Found: C, 60.17; H, 5.95; N, 11.97%. $C_{23}H_{24}N_4O_2 \cdot 2HCl$ requires C, 59.87; H, 5.68; N, 12.14%.

EXAMPLE 12

2-(1-[Benzo[b]thiophen-3-ylmethyl]piperid-4-yl)-1H-isoindole-1,3-(2H)-dione.

4-Phthalimidopiperidine, hydrochloride (1.33 g, 5 mmol) was suspended in dimethylformamide (12 cm$^3$) and triethylamine (1.5 g, 14.8 mmol) was added with stirring, followed by 3-bromomethylbenzo[b]thiophene (1.2 g, 5.3 mmol). After stirring for 4½ hours at room temperature a further small quantity of 3-bromomethylbenzo[b]thiophene was added. Stirring was continued for 2 hours then the reaction mixture was poured into water and the precipitated solid collected and dried (1.65 g, 87.8%).

The base was suspended in isopropyl alcohol, ethanolic HCl was added and the mixture stirred at room temperature overnight. The solid was collected, triturated with methanol under reflux and undissolved material filtered off. The filtrate was diluted with water until just turbid, then the methanol evaporated to give solid material suspended in water. The title compound as the monohydrochloride salt was collected and recrystallised from ethanol, then ethanol/methanol. (m.p = 163°–168° C.).

Analysis: Found C, 62.21; H, 5.75; N, 6.00%. $C_{22}H_{20}N_2O_2S \cdot HCl \cdot \frac{3}{4}H_2O$ requires C, 61.96; H, 5.32; N, 6.57%.

EXAMPLE 13

2-(1-[5-Methoxyindol-3-ylmethyl]piperid-4-yl)-1H-isoindole-1,3-(2H)-dione

5-Methoxyindole (1.0 g, 6.73 mmol) was dissolved in glacial acetic acid (8 cm³). 4-phthalimidopiperidine hydrochloride (1.79 g, 6.72 mmol), sodium acetate (0.59 g, 7.2 mmol) and formaldehyde (0.5 cm³, 40% aq w/v, 6.7 mmol) were added in that order to the stirred mixture. Stirring was continued at room temperature for 5 hours, then the mixture was poured into water, filtered, and the filtrate basified by addition of conc. ammonia. The precipitated solid was collected and dried (1.07 g, 41%).

The base was suspended in a small volume of boiling ethanol, and ethanolic HCl added to give a solution. Cooling overnight at 5° C. gave a gum. The mother-liquors were decanted and maintained at 5° C. for 3 weeks to give title compound as the hydrochloride, m.p. 178°–180° C.

Analysis: Found: C, 62.98; H, 5.73; N, 9.22%. $C_{23}H_{23}N_3,HCl.\frac{3}{4}H_2O$ requires C, 62.87; H, 5.85; N, 9.57%.

EXAMPLE 14

Repeating the procedure of Example 2 the following indolyl derivatives of formula I may be prepared according to the reaction scheme:

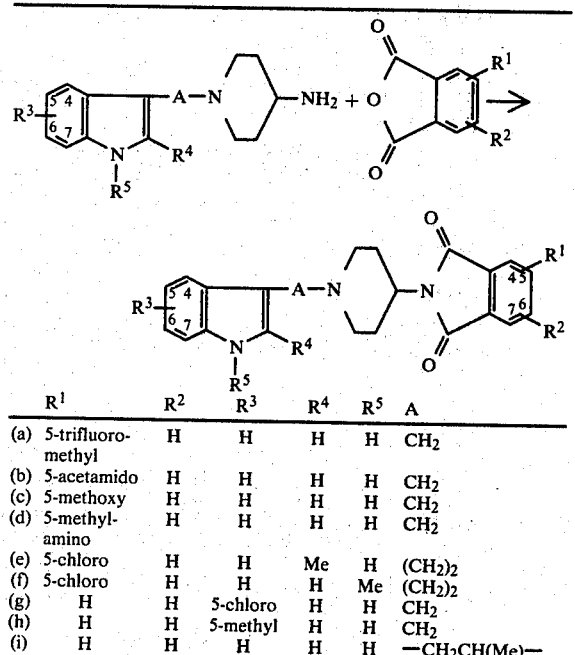

| | $R^1$ | $R^2$ | $R^3$ | $R^4$ | $R^5$ | A |
|---|---|---|---|---|---|---|
| (a) | 5-trifluoromethyl | H | H | H | H | $CH_2$ |
| (b) | 5-acetamido | H | H | H | H | $CH_2$ |
| (c) | 5-methoxy | H | H | H | H | $CH_2$ |
| (d) | 5-methylamino | H | H | H | H | $CH_2$ |
| (e) | 5-chloro | H | H | Me | H | $(CH_2)_2$ |
| (f) | 5-chloro | H | H | H | Me | $(CH_2)_2$ |
| (g) | H | H | 5-chloro | H | H | $CH_2$ |
| (h) | H | H | 5-methyl | H | H | $CH_2$ |
| (i) | H | H | H | H | H | $-CH_2CH(Me)-$ |

EXAMPLE 15

5,6-Dichloro-2-(1-[2-(indol-3-yl)ethyl]piperid-4-yl)-1H isoindole-1,3-(2H)-dione 4-Amino-1-[2-(indol-3-yl)ethyl]piperidine (3.64 g, 15 mmol) was dissolved in hot methyl cyanide (50 cm³) and 4,5-dichlorophthalic anhydride (3.25 g, 15 mmol) in hot methyl cyanide (30 cm³) was added dropwise with stirring to precipitate a solid. The mixture was stirred overnight. The solid was collected by filtration, pressed dry on a filter, and suspended in acetic anhydride (70 ml). The mixture was heated on a steam bath for 3 hours then the solvent was evaporated to give a bright yellow solid residue. Ethanol was added and evaporated twice to remove acetic anhydride. The solid was dissolved in very dilute aqueous acetic acid and re-precipitated as a gum by addition of conc. ammonia. The gum hardened on standing in ice.

The crude material (1 g) was suspended in ethanol (15 cm³) and methanesulphonic acid (0.15 cm³, 2.31 mmol) was added. The mixture was heated and stirred under reflux for 2 hours. The suspension was cooled briefly in ice and the solid collected. This was triturated at reflux with 9:1 ethanol:water then 9:1 methanol:water to give the title compound as the methanesulphonate salt, m.p. >270° C. (dec.).

Analysis: Found: C, 52.72; H, 5.03; N, 7.38%; $C_{22}H_{21}Cl_2N_3O_2.CH_3SO_3H.\frac{1}{2}H_2O$ requires: C, 52.65; H, 4.79; N, 7.67%.

EXAMPLE 16

5-Chloro-2-[1-(indol-3-ylmethyl)piperid-4-yl]-1H-isoindole-1,3-(2H)-dione

A solution of 5-chloro-2-ethoxycarbonyl-1H-isoindole-1,3-(2H)-dione (1.27 g, 5.01 mmol) in hot ethanol (20 cm³) was added rapidly with stirring to a solution of 4-amino-1-[1-indol-3-ylmethyl]piperidine (1.15 g, 5.02 mmol) in ethanol (10 cm³), giving a clear solution. This was refluxed for 3 hours, cooled overnight and the solid collected and dried. The mother-liquors were refluxed for a further 1.8 hours and a further crop of product recovered.

The product was suspended in isopropyl alcohol at reflux and acidified with ethanolic HCl, filtered, and the filtrate cooled in ice to give the title compound as the hydrochloride, m.p. 188°–190° C.

Analysis: Found: C, 59.95; H, 5.20; N, 9.33%; $C_{22}H_{20}ClN_3O_2.HCl.\frac{1}{2}H_2O$ requires: C, 60.15; N, 5.05; N, 9.56%.

EXAMPLE 17

5-Amino-2-[1-(indol-3-ylmethyl)piperid-4-yl]-1H-isoindole-1,3-(2H)-dione

5-Nitro-2-[1-(indol-3-ylmethyl)piperid-4-yl]-1H-isoindole-1,3-(2H)-dione (0.8 g, 1.98 mmol) was hydrogenated in methanol over Pd/C (5%, 0.15 g) at atmospheric pressure. The catalyst was filtered off and the filtrate evaporated. The solid product was recrystallised from chloroform to give the title compound.

I claim:

1. A compound of the formula:

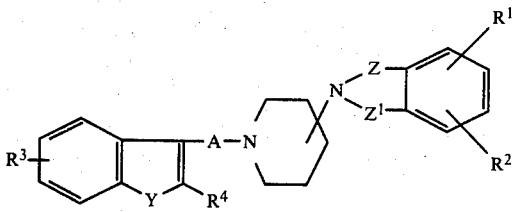

or a pharmaceutically acceptable acid addition or quaternary ammonium salt thereof, wherein the piperidine ring is substituted in the 3- or 4-position and in which Y is $-NR^5-$, $-O-$ or $-S-$, where $R^5$ is hydrogen or alkyl of 1 to 6 carbon atoms;

A is alkylene of 1 to 6 carbon atoms or hydroxyalkylene of 1 to 6 carbon atoms;

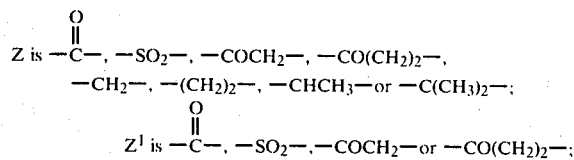

R¹, R² and R³ are, independently, hydrogen, halogen, alkyl of 1 to 6 carbon atoms, alkoxy of 1 to 6 carbon atoms, nitro, amino, alkylamino of 1 to 6 carbon atoms trifluoromethyl, alkanoylamino of 2 to 6 carbon atoms, hydroxy, or phenylalkoxy of 7 to 12 carbon atoms:

or R¹ and R² taken together with adjacent carbon atoms to which they are attached form a six membered carbocyclic ring; and R⁴ is hydrogen or alkyl of 1 to 6 carbon atoms; with the proviso that when A is —CH₂— R¹ and R² are other than nitro.

2. A compound of claim 1 in which A is a straight chain alkylene moiety of 1 to 4 carbon atoms.

3. A compound of claim 1 in which Y is —NH—.

4. A compound as claimed in claim 1 wherein Z represents —CO— and Z¹ represents —CO— or —SO₂—.

5. A compound as claimed in claim 1 which is 2-(1-[indol-3-ylmethyl]piperid-4-yl)-1H-isoindole-1,3-(2H)-dione.

6. A compound as claimed in claim 1 which is 2-(1-[2-(indol-3-yl)ethyl]piperid-4-yl)-1H-isoindol-1,3-(2H)-dione.

7. A compound as claimed in claim 1 which is 2-(1-[indol-3-ylmethyl]piperid-4-yl)-1,2-benzisothiazolin-3-one-1,1-dioxide.

8. A compound as claimed in claim 1 which is 2-[1-(2-[indol-3-yl]ethyl)piperid-4-yl]-1,3-(2H,4H)-isoquinolinedione.

9. A compound as claimed in claim 1 which is 2,3-dihydro-2-[1-(indol-3-ylmethyl)piperid-4-yl]-1H-isoindol-1-one.

10. A compound as claimed in claim 1 which is 5,6-benzo-2-(1-[2-(indol-3-yl)ethyl]piperid-4-yl)-1H-isoindol-1,3-(2H)-dione.

11. A compound as claimed in claim 1 which is 2-[1-(3-[indol-3yl]propyl)piperid-4-yl]-1H-isoindole-1,3-(2H)-dione.

12. A compound as claimed in claim 1 which is 5-chloro-2-(1-[2-(indol-3-yl)ethyl]piperid-4-yl)-1H-isoindole-1,3-(2H)-dione.

13. A compound as claimed in claim 1 which is 2-[1-(2-[indol-3-yl]ethyl)piperid-4-yl]-5-methyl-1H-isoindole-1,3-(2H)-dione.

14. A compound as claimed in claim 1 which is 2-[1-(2-[indol-3-yl]ethyl)piperid-4-yl]-5-nitro-1H-isoindole-1,3-(2H)-dione.

15. A compound as claimed in claim 1 which is 5-amino-2-(1-[2-(indol-3-yl)ethyl]-piperid-4-yl)-1H-isoindole-1,3-(2H)-dione.

16. A compound as claimed in claim 1 which is 2-(1-[benzo[b]thiophen-3-ylmethyl]piperid-4-yl)-1H-isoindole-1,3-(2H)-dione.

17. A compound as claimed in claim 1 which is 2-(1-[5-methoxyindol-3-ylmethyl]piperid-4-yl)-1H-isoindole-1,3-(2H)-dione.

18. A compound as claimed in claim 1 which is 5,6-dichloro-2-(1-[2-(indol-3-yl)ethyl]piperid-4-yl)-1H-isoindole-1,3-(2H)-dione.

19. A compound as claimed in claim 1 which is 5-chloro-2-[1-(indol-3-ylmethyl)piperid-4-yl]-1H-isoindole-1,3-(2H)-dione.

20. A compound as claimed in claim 1 which is 5-amino-2-[1-(indol-3-ylmethyl)piperid-4-yl]-1H-isoindole-1,3-(2H)-dione.

21. An antidepressant composition comprising an antidepressant amount of a compound of the formula:

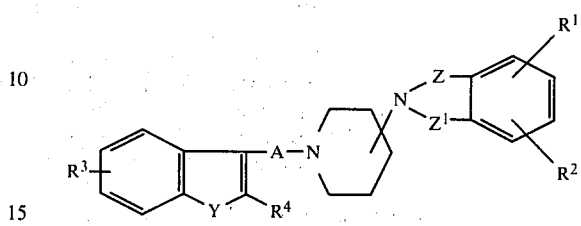

or a pharmaceutically acceptable acid addition or quaternary ammonium salt thereof, wherein the piperidine ring is substituted in the 3- or 4-position and in which Y is —NR⁵—, —O—, or —S—, where R⁵ is hydrogen or alkyl of 1 to 6 carbon atoms;

A is alkylene of 1 to 6 carbon atoms or hydroxyalkylene of 1 to 6 carbon atoms;

Z is

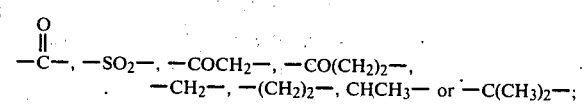

Z¹ is

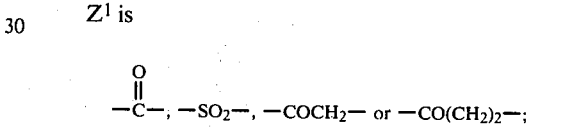

R¹, R² and R³ are, independently, hydrogen, halogen, alkyl of 1 to 6 carbon atoms, alkoxy of 1 to 6 carbon atoms, nitro, amino, alkylamino of 1 to 6 carbon atoms, trifluoromethyl, alkanoylamino of 2 to 6 carbon atoms, hydroxy, or phenylalkoxy of 7 to 12 carbon atoms;

or

R¹ and R² taken together with adjacent carbon atoms to which they are attached form a six membered carbocyclic ring;

and

R⁴ is hydrogen or alkyl of 1 to 6 carbon atoms; with the proviso that when A is —CH₂—, R¹ and R² are other than nitro;

and a pharmaceutically acceptable carrier.

22. An antidepressant composition of claim 21 in which said compound is 2-(1-[indol-3-ylmethyl]piperid-4-yl)-1H-isoindole-1,3-(2H)-dione or a pharmaceutically acceptable acid addition or quaternary ammonium salt thereof.

23. An antidepressant composition of claim 21 in which said compound is 2-(1-[2-(indol-3-yl)ethyl]piperid-4-yl)-1H-isoindol-1,3-(2H)-dione or a pharmaceutically acceptable acid addition or quaternary ammonium salt thereof.

24. An antidepressant composition of claim 21 in which said compound is 5-chloro-2-(1-[2-(indol-3-yl)ethyl]piperid-4-yl)-1H-isoindole-1,3-(2H)-dione or a pharmaceutically acceptable acid addition or quaternary ammonium salt thereof.

25. An antidepressant composition of claim 21 in which said compound is 5-amino-2-(1-[2-(indol-3-yl)ethyl]piperid-4-yl)-1H-isoindole-1,3-(2H)-dione or a pharmaceutically acceptable acid addition or quaternary ammonium salt thereof.